US012324433B2

(12) United States Patent
Josephson et al.

(10) Patent No.: US 12,324,433 B2
(45) Date of Patent: *Jun. 10, 2025

(54) ANTIMICROBIAL ENHANCEMENT OF CATIONIC ACTIVE SKIN ANTISEPTICS

(71) Applicant: ECOLAB USA INC., Saint Paul, MN (US)

(72) Inventors: Lilian Lam Josephson, Saint Paul, MN (US); Daniel E. Pedersen, Saint Paul, MN (US); Dale Curtis Larson, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 2 days.

This patent is subject to a terminal disclaimer.

(21) Appl. No.: 18/405,767

(22) Filed: Jan. 5, 2024

(65) Prior Publication Data

US 2024/0138407 A1 May 2, 2024

Related U.S. Application Data

(63) Continuation of application No. 15/929,716, filed on May 18, 2020, now Pat. No. 11,889,832.

(60) Provisional application No. 62/849,463, filed on May 17, 2019.

(51) Int. Cl.

*A01N 37/46* (2006.01)
*A01N 25/16* (2006.01)
*A01N 33/12* (2006.01)
*A01N 37/52* (2006.01)

(52) U.S. Cl.

CPC ............. *A01N 37/46* (2013.01); *A01N 25/16* (2013.01); *A01N 33/12* (2013.01); *A01N 37/52* (2013.01)

(58) Field of Classification Search

CPC ........ A01N 33/12; A01N 25/16; A01N 37/46; A01N 37/52

See application file for complete search history.

(56) References Cited

U.S. PATENT DOCUMENTS

| | | | |
|---|---|---|---|
| 4,320,147 A | 3/1982 | Schaeufele | |
| 5,389,685 A | 2/1995 | Smith et al. | |
| 5,545,749 A | 8/1996 | Smith et al. | |
| 5,547,990 A | 8/1996 | Hall et al. | |
| 5,833,741 A | 11/1998 | Walker | |
| 6,339,057 B1 | 1/2002 | Knox et al. | |
| 6,464,764 B1 | 10/2002 | Lichtenberg et al. | |
| 6,511,950 B1 | 1/2003 | Jenevein | |
| 6,583,181 B1 | 6/2003 | Chiang et al. | |
| 6,939,840 B2 | 9/2005 | Lichtenberg et al. | |
| 8,221,733 B2 | 7/2012 | Lichtenberg et al. | |
| 8,623,935 B2 | 1/2014 | Hobbs et al. | |
| 8,951,582 B2 | 2/2015 | Fusco | |
| 8,962,662 B2 | 2/2015 | Busch et al. | |
| 9,314,028 B2 | 4/2016 | Worthington et al. | |
| 9,380,784 B2 | 7/2016 | Derby et al. | |
| 9,920,284 B2 | 3/2018 | Sutton, Jr. et al. | |
| 9,926,511 B2 | 3/2018 | Valencia Sil et al. | |
| 10,206,392 B2 | 2/2019 | Kloeppel et al. | |
| 10,285,400 B2 | 5/2019 | Lei et al. | |
| 11,889,832 B2 * | 2/2024 | Josephson | A61Q 19/10 |
| 2003/0029812 A1 | 2/2003 | Burns et al. | |
| 2003/0114342 A1 | 6/2003 | Hall | |
| 2003/0187073 A1 | 10/2003 | Lichtenberg et al. | |
| 2004/0167046 A1 | 8/2004 | Lukenbach et al. | |
| 2004/0220275 A1 | 11/2004 | Lutzeler et al. | |
| 2005/0124723 A1 | 6/2005 | Fritschi et al. | |
| 2012/0070341 A1 | 3/2012 | Eder et al. | |
| 2013/0217788 A1 | 8/2013 | Kempers et al. | |
| 2014/0171512 A1 | 6/2014 | Kloeppel et al. | |
| 2016/0030315 A1 | 2/2016 | Emiru et al. | |
| 2016/0058004 A1 | 3/2016 | Callahan et al. | |
| 2017/0284605 A1 | 10/2017 | Janak et al. | |
| 2018/0087009 A1 | 3/2018 | Man et al. | |
| 2019/0191704 A1 | 6/2019 | ALbright et al. | |
| 2020/0229435 A1 | 7/2020 | Malet et al. | |
| 2020/0305437 A1 | 10/2020 | McGeechan et al. | |

FOREIGN PATENT DOCUMENTS

| | | |
|---|---|---|
| EP | 2739715 B1 | 6/2016 |
| GB | 2497389 A | 6/2013 |
| GB | 2501341 B | 10/2014 |
| GB | 2533527 B | 10/2018 |
| WO | 0035283 A1 | 6/2000 |
| WO | 0059696 A2 | 10/2000 |
| WO | 2008049616 A1 | 5/2008 |

(Continued)

OTHER PUBLICATIONS

Rios-Castillo et al., "Bactericidal Efficacy of Hydrogen Peroxide-Based Disinfectants Against Gram-Positive and Gram-Negative Bacteria on Stainless Steel Surfaces", Journal of Food Science, vol. 82, No. 10, pp. 2351-2356, Aug. 2017.

(Continued)

*Primary Examiner* — Johann R Richter
*Assistant Examiner* — Danielle Johnson
(74) *Attorney, Agent, or Firm* — McKee, Voorhees & Sease, PLC

(57) ABSTRACT

The disclosure relates to antimicrobial compositions and their methods of use and manufacture. In particular, the antimicrobial compositions described herein comprise an antimicrobial active, a primary foaming agent, and an L-amino acid to provide rapid antimicrobial efficacy. In a preferred embodiment, the antimicrobial compositions are dermal cleansers. In a most preferred embodiment, the antimicrobial compositions comprise a foam structure enhancing agent.

16 Claims, 2 Drawing Sheets

(56) References Cited

FOREIGN PATENT DOCUMENTS

| | | | |
|---|---|---|---|
| WO | 2017204727 | A1 | 11/2017 |
| WO | 2018044840 | A1 | 3/2018 |

OTHER PUBLICATIONS

International Searching Authority in connection with PCT/US2020/033409 filed May 18, 2020, "The International Search Report and the Written Opinion of the International Searching Authority, or the Declaration", 14 pages, mailed Aug. 27, 2020.

* cited by examiner

ANTIMICROBIAL ENHANCEMENT OF CATIONIC ACTIVE SKIN ANTISEPTICS

CROSS-REFERENCE

This application is a Continuation of U.S. Ser. No. 15/929,716, filed May 18, 2020, (now U.S. Pat. No. 11,889,832) which is related to and claims priority under 35 U.S.C. § 119 to U.S. Provisional Application Ser. No. 62/849,463 filed on May 17, 2019, and entitled "ANTIMICROBIAL ENHANCEMENT OF CATIONIC ACTIVE SKIN ANTISEPTICS"; the entire contents of this patent application are hereby expressly incorporated herein by reference.

FIELD OF THE INVENTION

The invention relates to antimicrobial compositions. In particular, antimicrobial hand wash compositions with fast acting antimicrobial character able to achieve multiple $Log_{10}$ reductions in 15 seconds.

BACKGROUND OF THE INVENTION

Antimicrobial hand soaps are an important component of maintaining public health by reducing the transfer of biological pathogens. Formulation of antimicrobial hand soaps is critical to ensure both acceptable user aesthetics including foam and feel during wash, as well as, the ability to reduce bacteria on skin. Moreover, the U.S. FDA is considering increasing the performance threshold required for antimicrobial soaps, by updating the passing requirements for the healthcare personnel hand wash method ASTM 1174. While some formulations may be able to meet these increased efficacy standards, many that may have sufficient antimicrobial efficacy are harsh on the skin, particularly if used repeatedly. An additional problem is that efficacious antimicrobial formulations can often have a deleterious effect on foaming properties, which are often desirable for hand washes. Further, new formulations, employing different antimicrobial compounds can often have unexpected interactions with other ingredients such that the compositions must be reformulated.

Traditional foaming agents are generally anionic surfactants. Amphoteric surfactants can be added to the primary anionic surfactant to increase foam height. Unfortunately, many commonly used foaming systems, particularly anionic surfactants, are incompatible with cationic active ingredients. Additionally, many surfactants may be chemically compatible with cationic active ingredients, but have a deleterious effect on the microbiological efficacy of the active. Currently, most formulations of this type rely on amine oxide-type surfactants. While amine oxide surfactant systems can provide acceptable foaming characteristics with some level of bactericidal activity, current amine oxide-based systems don't possess sufficient microbiocidal activity to meet the new requirements being proposed by the FDA without a high level of active ingredient. Further, when amine oxide levels are increased, they can act as a skin irritant. This has made inclusion of amine oxides at a sufficient active concentration undesirable. Alternative microbiocidal active components have also included chlorhexidine gluconate (CHG). Typical CHG systems require about 4% active concentration to achieve desired microbiocidal activity. This too can result in skin irritation.

Thus, new antimicrobial hand wash compositions are needed; particularly those that have increased antimicrobial efficacy and acceptable skin compatibility. Further, it has been found that formulating antimicrobial handwash compositions comprising a quaternary ammonium compound as an antimicrobial active with foaming surfactants that do not inhibit the cidal activity of the quaternary ammonium compound is critical to antimicrobial performance.

Accordingly, it is an objective of the claimed invention to provide antimicrobial compositions having increased antimicrobial efficacy.

A further object of the invention is to provide antimicrobial compositions that are dermally compatible with acceptable use aesthetics.

Yet another object of the invention is to provide antimicrobial compositions that have lower active concentrations of the microbiocidal component while maintaining or increasing antimicrobial efficacy.

Other objects, advantages and features of the present invention will become apparent from the following specification taken in conjunction with the accompanying figure.

BRIEF SUMMARY OF THE PREFERRED EMBODIMENT

An advantage of the present antimicrobial compositions is that they provide improved antimicrobial efficacy while being dermally compatible. Yet another advantage of the antimicrobial compositions is that they maintain desired foaming properties while providing improved antimicrobial efficacy.

A preferred embodiment includes an antimicrobial composition comprising from about 0.01 wt. % to about 2 wt. % of an antimicrobial active compound comprising one or more of the following benzalkonium chloride, benzethonium chloride, dialkyl dimethyl ammonium chlorides, chlorhexidine gluconate, and mixtures thereof, wherein the antimicrobial active compound has antimicrobial activity toward Gram positive and/or Gram negative microorganisms; from about 0.1 wt. % to about 5 wt. % of a primary foaming agent, wherein the primary foaming agent comprises a C8-C16 alkanolamide, a glucosamide, or a mixture thereof; from about 5 mM to about 150 mM of an L-amino acid, wherein the L-amino acid is an aliphatic L-amino acid, amide L-amino acid, or basic amino acid; and from about 65 wt. % to about 99.7 wt. % of a carrier; wherein the composition has a pH between about 6 and about 9.6.

A further preferred embodiment an antimicrobial composition comprising from about 0.01 wt. % to about 2 wt. % of an antimicrobial active compound comprising one or more of the following benzalkonium chloride, benzethonium chloride, dialkyl dimethyl ammonium chloride, chlorhexidine gluconate, and mixtures thereof, wherein the antimicrobial active compound has antimicrobial activity toward Gram positive and/or Gram negative microorganisms; from about 0.1 wt. % to about 5 wt. % of a primary foaming agent, wherein the primary foaming agent comprises a C8-C16 alkanolamide, a glucosamide, or a mixture thereof; from about 5 mM to about 150 mM of an L-amino acid, wherein the L-amino acid is an aliphatic L-amino acid, amide L-amino acid, or basic amino acid; from about 0.1 wt. % and about 2 wt. % of a C8-C12 Guerbet alcohol ethoxylate; and from about 65 wt. % to about 99.7 wt. % of a carrier; wherein the composition has a pH between about 6 and about 9.6.

Another preferred embodiment is a method of cleaning a surface comprising contacting a surface with an antimicrobial composition, wherein the antimicrobial composition comprises from about 0.01 wt. % to about 2 wt. % of an antimicrobial active compound comprising one or more of the following benzalkonium chloride, benzethonium chloride, chlorhexidine gluconate, and mixtures thereof, wherein the antimicrobial active compound has antimicrobial activity toward Gram positive and/or Gram negative microorganisms; from about 0.1 wt. % to about 5 wt. % of a primary foaming agent, wherein the primary foaming agent comprises a C8-C16 alkanolamide, a glucosamide, or a mixture thereof; from about 5 mM to about 150 mM of an L-amino acid, wherein the L-amino acid is an aliphatic L-amino acid, amide L-amino acid, or basic amino acid; and from about 65 wt. % to about 99.7 wt. % of a carrier; wherein the composition has a pH between about 6 and about 9.6.

Still another preferred embodiment is a method of cleaning a surface comprising contacting a surface with an antimicrobial composition, wherein the antimicrobial composition comprises from about 0.01 wt. % to about 2 wt. % of an antimicrobial active compound comprising one or more of the following benzalkonium chloride, benzethonium chloride, chlorhexidine gluconate, and mixtures thereof, wherein the antimicrobial active compound has antimicrobial activity toward Gram positive and/or Gram negative microorganisms; from about 0.1 wt. % to about 5 wt. % of a primary foaming agent, wherein the primary foaming agent comprises a C8-C16 alkanolamide, a glucosamide, or a mixture thereof; from about 5 mM to about 150 mM of an L-amino acid, wherein the L-amino acid is an aliphatic L-amino acid, amide L-amino acid, or basic amino acid; from about 0.1 wt. % and about 2 wt. % of a C8-C12 Guerbet alcohol ethoxylate; and from about 65 wt. % to about 99.7 wt. % of a carrier; wherein the composition has a pH between about 6 and about 9.6.

While multiple embodiments of the antimicrobial compositions are disclosed, still other embodiments may become apparent to those skilled in the art from the following detailed description, which shows and describes illustrative embodiments of the invention. Accordingly, the detailed description, exemplary embodiments, and working examples are to be regarded as illustrative in nature and not restrictive.

Figure 1:
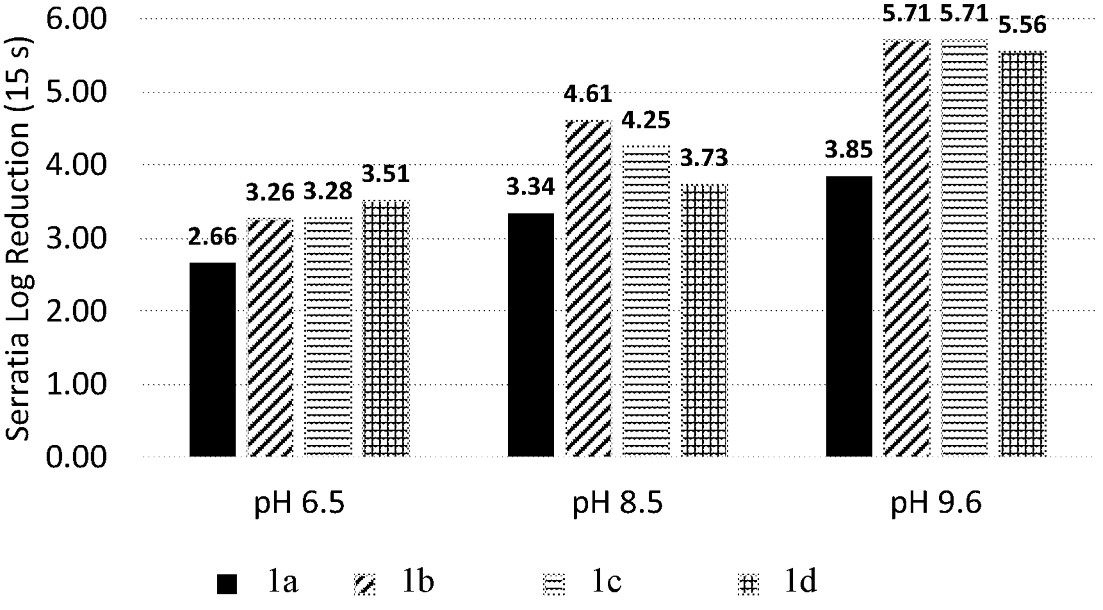
FIG. 1 shows a bar graph comparing the antimicrobial performance of an exemplary antimicrobial composition containing no amino acid against various exemplary antimicrobial compositions containing an amino acid at pH levels of 6.5, 8.5, and 9.6 and a 15 second contact time. The Figure is representative of the data provided in Table 2 of Example 1.

Various embodiments of the present invention will be described in detail with reference to the figures. Reference to various embodiments does not limit the scope of the invention. Figures represented herein are not limitations to the various embodiments do not limit the scope of the invention.

DETAILED DESCRIPTION OF THE PREFERRED EMBODIMENT

The embodiments of antimicrobial compositions are not limited to particular methods of preparation or use, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations. Whether or not modified by the term "about," the claims include equivalents to the quantities.

The methods and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

The term "actives" or "percent actives" or "percent by weight actives" or "actives concentration" are used interchangeably herein and refers to the concentration of those ingredients involved in cleaning expressed as a percentage minus inert ingredients such as water or salts. It is also sometimes indicated by a percentage in parentheses, for example, "chemical (10%)."

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Use of the term antimicrobial "-cidal" effect or activity, refers to a lethal, irreversible action resulting in complete microbial cell destruction or incapacitation.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism or infective protein. Microorganisms include all prokaryotes. Microorganisms include bacteria (including cyanobacteria), spores, lichens, fungi, yeasts, protozoa, virinos, viroids, viruses, phages, and some algae. As used herein, the term "microbe" is synonymous with microorganism.

The term "surfactant" refers to a molecule having surface activity, including wetting agents, dispersants, emulsifiers, detergents, and foaming agents, and the like. It is understood to be inclusive of the use of a single surfactant or multiple surfactants.

The term "weight percent," "wt. %," "wt-%," "percent by weight," "% by weight," and variations thereof, as used herein, refer to the concentration of a substance as the weight of that substance divided by the total weight of the composition and multiplied by 100.

For the purpose of this patent application, successful microbial reduction is achieved when the microbial populations are reduced by at least about 0.5 log, or by significantly more than is achieved by a wash with water. Larger reductions in microbial population provide greater levels of protection.

As used herein, the term "soil" or "stain" refers to a non-polar oily substance which may or may not contain particulate matter such as mineral clays, sand, natural mineral matter, carbon black, graphite, kaolin, environmental dust, etc.

As used herein, the term "substantially free" refers to compositions completely lacking the component or having such a small amount of the component that the component does not affect the performance of the composition. The component may be present as an impurity or as a contaminant and shall be less than 0.1 wt-%. In another embodiment, the amount of the component is less than 0.05 wt-% and in yet another embodiment, the amount of component is 0 wt-%.

As used herein, the phrase "water soluble" means that the material is soluble in water in the present composition. In general, the material should be soluble at 25° C. at a concentration of between about 0.1 wt. % and about 15 wt. % of the water, more preferably at a concentration of between about 0.1 wt. % and about 10 wt. %.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods, systems, apparatuses, and compositions described herein may comprise, consist essentially of, or consist of the components and ingredients as well as other ingredients. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

Compositions

The antimicrobial compositions described herein have been found to maintain or improve antimicrobial efficacy while being in active concentrations lower than many existing antimicrobial actives such as CHG. Surprisingly, the antimicrobial compositions described herein provide improved efficacy and cidal activity in a shorter time period than existing compositions. Additionally, the antimicrobial compositions described herein have been found to be dermally compatible and less irritating than existing products that provide the same level of microbiocidal efficacy.

Many surfactants inhibit the microbiological efficacy of cationic active ingredients such benzalkonium chloride, benzethonium chloride, and chlorhexidine organic or sugar salts including chlorhexidine gluconate. Thus, it has proven difficult to formulate cleaning compositions with cationic active ingredients that retain antimicrobial activity, provide adequate foaming characteristics, and possess acceptable skin compatibility. Moreover, as antimicrobial performance thresholds continue to be raised, the difficulty of formulating compositions meeting the performance requirements has become increasingly difficult. Thus, the compositions of the invention seek to solve these problems as well as other problems identified herein or others recognized in the art.

For example, amine oxides were also found to provide desired foaming and antimicrobial properties, but tend to be harsher on skin at higher concentrations. Thus, they can be employed, but it has been found that a lesser concentration can be preferred for embodiments with prolonged or repeated skin contact. Alkyl polyglucosides (APGs) were found to have moderate foaming and antimicrobial properties, but desired skin compatibility. Betaines were found to provide desired foaming, poor antimicrobial properties, and moderate skin compatibility. Based on these findings, it was determined that the primary foaming agent is preferably a C8-C16 alkanolamide, a glucamide, or mixture thereof. Betaines and APGs can be included in the compositions in lesser concentrations, but are preferably absent from the compositions.

Unexpectedly, it has been found that incorporating an L-amino acid, a Guerbet alcohol ethoxylate or both an L-amino acid and Guerbet alcohol ethoxylate, the antimicrobial efficacy is greatly improved providing multiple log reductions in 15 seconds. Some embodiments have been found to provide unexpected synergistic antimicrobial properties including the cidal properties and speed of cidal activity.

In a preferred embodiment, the compositions comprise an antimicrobial active, a primary foaming agent, a carrier, and an L-amino acid. In a preferred embodiment, the compositions comprise an antimicrobial active, a primary foaming agent, a carrier, and a Guerbet alcohol ethoxylate. In a most preferred embodiment, the compositions comprise an antimicrobial active, a primary foaming agent, a carrier, an L-amino acid, and a Guerbet alcohol ethoxylate. These compositions can also comprise a variety of optional additional ingredients, including, but not limited to, a chelant, a dye, an emollient, a foam structure enhancer, a fragrance, a humectant, a preservative, a secondary foaming agent, or combination thereof.

L-Amino Acid

The compositions comprise one or more L-amino acids. Preferably the L-amino acids are aliphatic, amide, or basic L-amino acids in their natural or salt form. Preferred amino acids include, but are not limited to, L-arginine, L-glutamine, L-glycine, L-histidine, L-leucine, and L-lysine, their salts and/or mixtures thereof. Surprisingly, we found that the inclusion of an L-amino acid results in synergistic performance of the antimicrobial compositions. In a preferred embodiment, the compositions contain less than 0.1 wt. %, 0.05 wt. %, 0.01 wt. %, or are free of an aromatic amino acid, sulfur amino acid, hydroxyl amino acid, and/or acidic amino acid.

The preferred concentrations of L-amino acid can be expressed in weight percentage or millimoles (mM). Preferably, at use dilution the compositions comprise from about 0.075 wt-% to about 2 wt-% L-amino acid, more preferably from about 0.1 wt-% to about 1.8 wt-% L-amino acid, and most preferably from about 0.2 wt-% to about 1.5 wt-% L-amino acid. Preferably, at use dilution the compositions comprise from about 5 mM to about 150 mM L-amino acid, more preferably from about 10 mM to about 120 mM L-amino acid, and most preferably from about 20 mM to about 100 mM L-amino acid.

Antimicrobial Active

The compositions comprise one or more antimicrobial active compounds, which have antimicrobial activity toward Gram positive and/or Gram negative microorganisms, including, preferably against *E. coli, S. marcescens,* and *S. aureus* (MRSA). Preferred antimicrobial active compounds include: benzalkonium chloride, benzethonium chloride, chlorhexidine gluconate, didecyldimethylamonium chloride, dialkyl dimethyl ammonium chlorides (including but not limited to (C8-C20 dialkyl dimethyl ammonium chlorides), and mixtures thereof.

Preferably, at use dilution the compositions comprise from about 0.01 wt-% to about 2 wt-% antimicrobial active, more preferably from about 0.05 wt-% to about 1.5 wt-% antimicrobial active, and most preferably from about 0.1 wt-% to about 4.0 wt-% antimicrobial active.

In a preferred embodiment, the antimicrobial active contains less than 0.1 wt. % triclosan (2,4,4'-trichloro-2'hydroxy-diphenylether), preferably less than 0.05 wt. % triclosan, and most preferably is free of triclosan.

Carrier

The compositions comprise one or more carriers. Preferred carriers can include, but are not limited to, water and/or water-soluble carriers. Preferred water-soluble carriers include, but are not limited to, alcohols, water soluble diols, or mixtures thereof. Preferred alcohols include, but are not limited to, ethanol, n-propanol, and isopropanol. Preferred diols include, but are not limited to, pentylene glycol, hexylene glycol and propylene glycol. In a preferred embodiment comprising water as a carrier, the water is deionized water or softened water.

The antimicrobial composition does not require a low pH or a high pH to provide a rapid reduction in microbial populations. Preferably the antimicrobial compositions have a pH of between about 6 and about 9.6, more preferably between about 6.5 and about 9, and most preferably between about 7 and about 8.5 Within this pH range, the antimicrobial compositions effectively reduce microbial populations, and are acceptable for dermal use.

Preferably, the use dilution compositions comprise from about 65 wt-% to about 99.7 wt-% carrier, more preferably from about 75 wt-% to about 99.5 wt-% carrier, and most preferably from about 80 wt-% to about 95 wt-% carrier.

Guerbet Alcohol Ethoxylate

In a preferred embodiment, the compositions optionally comprise a Guerbet alcohol ethoxylate. Preferred Guerbet alcohol ethoxylates are C8-C12 Guerbet alcohol ethoxylates. Preferred C8-C12 Guerbet alcohol ethoxylates include, but are not limited to, PEG-3 ethylhexyl ether, PEG-6 ethylhexyl ether, PEG-9 ethylhexyl ether, PEG-3 propylheptyl ether, PEG-5 propylheptyl ether, PEG-6 propylheptyl ether, PEG-9 propylheptyl ether, PEG-6 butyloctyl ether, PEG-9 butyloctyl ether, and mixtures thereof.

Preferably, the use dilution compositions comprise from about 0.1 wt-% to about 2 wt-% Guerbet alcohol ethoxylate, more preferably from about 0.3 wt-% to about 1.5 wt-% Guerbet alcohol ethoxylate, and most preferably from about 0.5 wt-% to about 1.5 wt-% Guerbet alcohol ethoxylate.

Primary Foaming Agent

The compositions comprise one or more primary foaming agents. Primary surfactants are responsible for the generation of foam volume. Preferred foaming agents include nonionic surfactants. Examples of nonionic primary surfactants include C8-C16 alkanolamides, glucosamides, and mixtures thereof. Each of these classes of surfactant provide adequate foam generation and do not have a significant negative impact on microbiological efficacy. In a preferred embodiment, the compositions comprise one or more primary foaming agents.

Preferred C8-C16 alkanolamides include, but are not limited to, cocamides, lauramides, myristamides, soyamides, and mixtures thereof. Preferred cocamides include, but are not limited to, cocamide diethanolamine, cocamide monoethanolamine, cocamide methyl monoethanolamine, cocamide monoisopropanol amine (MIPA), and cocamide diisopropanolamine (DIPA), and mixtures thereof. Preferred lauramides include, but are not limited to, lauramide MEA, lauramide DEA, lauramide MIPA, and mixtures thereof. Preferred myristamides include, but are not limited to, myristamide MEA, myristamide DEA, and mixtures thereof. A preferred soyamide is soyamide DEA.

Preferred glucosamides are those having less than 18 carbons in the alkyl chain. More preferred are C8-C16 glucosamides which include, but are not limited to, capryloyl/caproyl methyl glucosamide, cocoyl methyl glucosamide, lauroyl/myristoyl methyl glucosamide, and mixtures thereof. Most preferred are glucosamides having between about 10 and about 14 carbons in the alkyl chain. A preferred glucosamide is lauroyl methyl glucosamide as shown in the formula below:

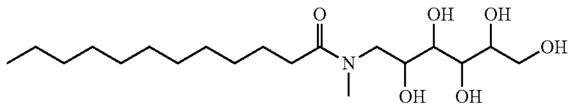

Lauroyl Methyl Glucamide

One surprising finding is that while glucosamides are suitable for the compositions, structurally similar surfactants such as widely used C8-C18 glucosides are not suitable. The inhibitory effect observed with C8-C18 glucosides, and the lack of a similar inhibitory effect with the C8-C18 glucosamide surfactants is surprising due to the high degree of structural similarity. The polar head group of the glucoside and glucosamide classes of surfactants are shown below. Head groups are depicted in their ring open state.

Glucoside Polar Head Group

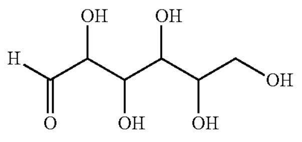 [SMILES: O=CC(O)C(O)C(O)C(O)CO]

Glucosamide Polar Head Group

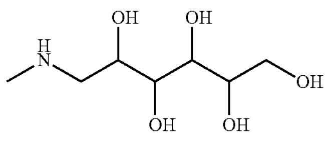

The compositions of the invention can comprise the primary foaming agent in a concentration of between about 0.1 wt. % and about 5 wt. %, preferably about 0.5 wt. % and about 4.5 wt. %, and more preferably between about 1.0 wt. % and about 4 wt. %.

Additional Ingredients

The antimicrobial compositions can include additional optional components. Often these components are added for functional benefits and/or properties. As such, in some embodiments, the antimicrobial composition including the antimicrobial active component, foaming surfactant, and carrier may provide a large amount, or even all of the total weight of the antimicrobial composition, for example, in embodiments having few or no additional functional materials disposed therein. The functional ingredients provide desired properties and functionalities to the antimicrobial composition. For the purpose of this application, the term "functional ingredients" include ingredients that when dispersed or dissolved in a use and/or concentrate solution, such as an aqueous solution, provide a beneficial property in a particular use. The antimicrobial compositions can optionally contain other chelants, disinfectants, dyes, emollients, foam structure enhancing agents, fragrances, pH modifiers, preservatives, sanitizers, secondary foaming agents, surfactants, and thickening or gelling agents. Some particular examples of additional functional ingredients are discussed in more detail below, but it should be understood the particular ingredients discussed below are given by way of example only, and that a broad variety of other functional ingredients may be used. For example, may of the functional material discussed below relate to materials used in disinfecting and/or cleansing applications, but it should be understood that other embodiments may include functional materials for use in other applications.

If included in the compositions, the additional optional ingredients are in an amount between about 0 wt. % and about 15 wt. %, more preferably between about 0 wt. % and about 12 wt. %, and most preferably 0.01 wt. % and about 10 wt. %.

Chelants

The compositions can optionally comprise one or more chelants. Preferred chelants, include, but are not limited to, phosphonic acid and phosphonates, phosphates, aminocarboxylates and their derivatives, pyrophosphates, ethylenediamine and ethylenetriamine derivatives, hydroxyacids, and mono-, di-, and tri-carboxylates and their corresponding acids. Other chelants include nitroloacetates and their derivatives, and mixtures thereof.

Examples of aminocarboxylates include amino acetates and salts thereof. Suitable amino acetates include: N-hydroxyethylaminodiacetic acid; hydroxyethylenediaminetetraacetic acid; nitrilotriacetic acid (NTA); ethylenediaminetetraacetic acid (EDTA), including its various salts; N-hydroxyethyl-ethylenediaminetriacetic acid (HEDTA); diethylenetriaminepentaacetic acid (DTPA); and alanine-N,N-diacetic acid; and methylglycine diacetic acid (MGDA); n-hydroxyethyliminodiacetic acid; and the like; their alkali metal salts; and mixtures thereof. Suitable aminophosphates include nitrilotrismethylene phosphates and other aminophosphates with alkyl or alkaline groups with less than 8 carbon atoms.

Exemplary polycarboxylates iminodisuccinic acids (IDS), sodium polyacrylates, citric acid, gluconic acid, oxalic acid, salts thereof, mixtures thereof, and the like. Additional polycarboxylates include citric or citrate-type chelating agents, polymeric polycarboxylate, and acrylic or polyacrylic acid-type chelating agents. Additional chelants include polyaspartic acid or co-condensates of aspartic acid with other amino acids, $C_4$-$C_{25}$-mono-or-dicarboxylic acids and $C_4$-$C_{25}$-mono-or-diamines Exemplary polymeric polycarboxylates include polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, and the like.

Preferred chelants include, EDTA, MGDA, and NTA. Most preferred chelants include EDTA and MGDA.

The addition of a chelant in antimicrobial compositions can provide increased efficacy against gram negative microorganisms. Surprisingly, however, it was found that certain chelating agents provided substantially increased efficacy against gram negative microorganisms while others provided little to no improvement. Glutamic acid diacetic acid (GLDA) is an amino acid-based chelating agent. It is well-known for its ability to boost the efficacy of biocides across a wide variety of formulation types, including personal care products. Surprisingly, the addition of GLDA to a base formula did not show any enhancement of antimicrobial efficacy. Methylglycinediacetic acid (MGDA), like GLDA, is an amino acid-containing chelating agent. Their structures are shown below:

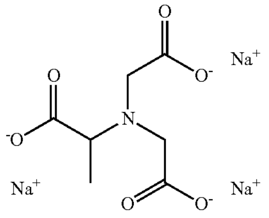

MGDA

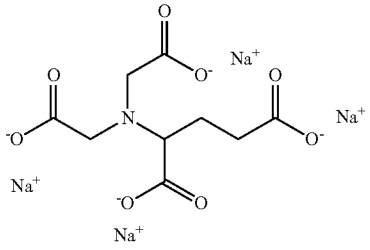

GLDA

Despite the structural similarities of these two compounds, the functional effect of the two compounds vary drastically. The addition of MGDA was found to significantly enhance the biocidal activity of the cationic active-containing base formula.

Traditional chelating agents, including EDTA, were also shown to have a positive impact on microbiological efficacy, particularly against gram negative organisms.

In a preferred use dilution embodiment containing an optional chelant, the compositions can comprise from about 0.01 wt-% to about 1 wt-% chelant, more preferably from about 0.05 wt-% to about 0.5 wt-% chelant, and most preferably from about 0.1 wt-% to about 0.4 wt-% chelant.

Dye

The composition may optionally include a dye. Examples of Ayes include any water soluble or product soluble dye, any FD&C or D&C approved dye, Emollient The compositions can optionally comprise one or more emollients. Preferred emollients, include, but are not limited to, capric/caprylic triglyceride, C12-15 alkyl benzoate, capric triglyceride, caprylic triglyceride, isopropyl myristrate, isopropyl palmitate, octyldodecanol, decyl oleate, cocoglycerides, ethylhexyl stearate, cetearyl isononanoate, cetearyl ethyhexanonate, decyl cocoate, cetyl dimethicone, ethylhexyl palmitate, PPG-11 stearyl ether, PPG-15 stearyl ether, PPG-14 butyl ether, dicaprylyl carbonate, dibutyl adipate, hexyl laurate, dicaprylyl ether, propylheptyl caprylate, isocetyl palmitate, hydrogentated polyisobutene, diethylhexylcarbonate, tocopheryl acetate, methyl gluceth-10, methyl gluceth-20, dicaprylyl carbonate, dibutyl adipate, hexyl laurate, dicaprylyl ether, propylheptyl caprylate, ethoxylated natural and synthetic oils, and mixtures thereof. Preferred emollients, include, but are not limited to, C12-15 alkyl benzoate, capric triglyceride, caprylic triglyceride, isopropyl myristrate, isopropyl palmitate, octyldodecanol, decyl oleate, cocoglycerides, ethylhexyl stearate, cetearyl isononanoate, cetearyl ethyhexanonate, decyl cocoate, cetyl dimethicone, ethylhexyl palmitate, PPG-11 stearyl ether, PPG-15 stearyl ether, PPG-14 butyl ether, and mixtures thereof.

When an emollient is included in the use dilution compositions, it is preferably in an amount from about 0.01 wt-% to about 1 wt-%, more preferably from about 0.05 wt-% to about 0.75 wt-%, and most preferably from about 0.1 wt-% to about 0.5 wt-%.

Foam Structure Enhancing Agent

In preferred embodiments, the compositions can optionally comprise one or more foam structure enhancing agents. Foam structure enhancing agents are agents that change the physical foam structure including foam stability, bubble size, density and rigidity thereby imparting sensorial attributes during the washing process. Users may describe such sensorial attributes as lather, creaminess, cushion, and/or slip. Preferred foam structure enhancing agents, include, but are not limited to, hexylene glycol, polyols, such as glycerol (glycerin), propylene glycol, propylene glycol n-alkanols, polyethylene glycols, other glycols and mixtures thereof.

When the compositions comprise an optional foam structure enhancing agent, it is preferably from about 0.01 wt-% to about 4 wt-% foam structure enhancing agent, more preferably from about 0.02 wt-% to about 3 wt-% foam structure enhancing agent, and most preferably from about 0.03 wt-% to about 2 wt-% foam structure enhancing agent.

In a preferred embodiment a novel foam structure agent is disclosed as a linear, non-substituted high molecular weight polyethylene glycol, such as PEG 300 or greater, or PEG 1000 or greater. In a particularly preferred embodiment, the PEG 8000 is the foam structure enhancing agent.

Examples of other foam structure enhancing agents include an organic solvent, other than a short chain alcohol, typically soluble in both water and oil. Examples of foam structure enhancing agents according to the present invention include: polyols, such as glycerol (glycerin), propylene glycol, hexylene glycol, propylene glycol n-alkanols, other glycols, monooleate of ethoxylated glycerides (with 8 to 10 ethylene oxide units); esters, such as isopropyl myristate/palmitate, myristyl alcohol, lauryl alcohol, lauryl lactate, amides, such as acetamide oleates such as triolein; According to one preferred embodiment the foam stabilizer is hexylene glycol.

The foam structure enhancing agents constituent may also comprise at least one a fatty alkanolamide, examples of which include but are not limited to: oleamide MIPA, stearamide MEA capramide DEA, ricinoleamide DEA, stearamide DEA, oleylamide DEA, tallowamide DEA, tallowamide MEA, isostearamide DEA, isostearamide MEA, and mixtures thereof. Alkanol amides may provide an ancillary thickening benefit as well. A preferred alkanol amide is diisopropanolamide, such as the Cola® liquid non-DEA amides available from Colonial chemical which includes cocamide DIPA (diisopropanolamide), Soyamide DIPA, lauramide DIPA, or myristamide DIPA.

In yet another preferred embodiment the composition includes diisopropanolamide as a part of the foam structure enhancing component. Diisopropanolamide may be present in the entire composition in an amount of from about 0.01 wt. % to about 8 wt. %, from about 0.05 wt. % to about 5 wt. % and more preferably from about 0.1 wt. % to about 3 wt. %.

Fragrance

The antimicrobial compositions can optionally comprise a fragrance. Examples of possible fragrances include natural oils or naturally derived materials, and synthetic fragrances such as hydrocarbons, alcohols, aldehydes, ketones, esters, lactones, ethers, nitriles, and polyfunctionals. Non-limiting examples of natural oils include the following: basil (*Ocimum basilicum*) oil, bay (*Pimento acris*) oil, bee balm (*Monarda didyma*) oil, bergamot (*Citrus aurantium bergamia*) oil, cardamom (*Elettaria cardamomum*) oil, cedarwood (*Cedrus atlantica*) oil, chamomile (*Anthemis nobilis*) oil, cinnamon (*Cinnamomum cassia*) oil, citronella (*Cymbopogon nardus*) oil, clary (*Salvia sclarea*) oil, clove (*Eugenia caryophyllus*) oil, cloveleaf (*Eufenia caryophyllus*) oil, *Cyperus esculentus* oil, cypress (*Cupressus sempervirens*) oil, *Eucalyptus citriodora* oil, geranium maculatum oil, ginger (*Zingiber officinale*) oil, grapefruit (*Citrus grandis*) oil, hazel (*Corylus avellana*) nut oil, jasmine (*Jasminum officinale*) oil, *Juniperus communis* oil, *Juniperus oxycedrus* tar, *Juniperus virginiana* oil, kiwi (*Actinidia chinensis*) water, lavandin (*Lavandula hybrida*) oil, lavender (*Lavandula angustifolia*) oil, lavender (*Lavandula angustifolia*) water, lemon (*Citrus medica limonum*) oil, lemongrass (*Cymbopogon schoenanthus*) oil, lime (*Citrus aurantifolia*) oil, linden (*Tilia cordata*) oil, linden (*Tilia cordata*) water, mandarin orange (*Citrus nobilis*) oil, nutmeg (*Myristica fragrans*) oil, orange (*Citrus aurantium dulcis*) flower oil, orange (*Citrus aurantium dulcis*) oil, orange (*Citrus aurantium dulcis*) water, patchouli (*Pogostemon cablin*) oil, peppermint (*Menthe piperita*) oil, peppermint (*Menthe peperita*) water, rosemary (*Rosmarinus officinalis*) oil, rose oil, rose (*Rosa damascena*) extract, rose (*Rosa multiflora*) extract, rosewood (*Aniba rosaeodora*) extract, sage (*Salvia officinalis*) oil, sandalwood (*Santalum album*) oil, spearmint (*Menthe viridis*) oil, tea tree (*Melaleuca alternifolia*) oil, and ylang ylang (*Cananga odorata*) oil. Some non-limiting examples of synthetic hydrocarbon fragrances include caryophyllene, β-farnesene, limonene, α-pinene, and β-pinene. Some non-limiting examples of synthetic alcohol fragrances include bacdanol, citronellol, linalool, phenethyl alcohol, and α-terpineol (R=H). Some non-limiting examples of synthetic aldehyde fragrances include 2-methyl undecanal, citral, hexyl cinnamic aldehyde, isocycolcitral, lilial, and 10-undecenal. Some non-limiting examples of synthetic ketone fragrances include cashmeran, α-ionone, isocyclemone E, koavone, muscone, and tonalide. Some non-limiting examples of synethetic ester fragrances include benzyl acetate, 4-t-butylcyclohexyl acetate (cis and trans), cedryl acetate, cyclacet, isobornyl acetate, and α-terpinyl acetate (R=acetyl). Some non-limiting examples of synthetic lactone fragrances include coumarin, jasmine lactone, muskalactone, and peach aldehyde. Some non-limiting examples of synthetic ether fragrances include ambroxan, anther, and galaxolide. Some non-limiting examples of synthetic nitrile fragrances include cinnamonitrile and gernonitrile. Finally, some non-limiting examples of synthetic polyfunctional fragrances include amyl salicylate, isoeugenol, hedione, heliotropine, lyral, and vanillin Preferably, in a use dilution composition, the fragrance is in a concentration between about 0 wt. % and about 1 wt. %, more preferably between about 0.01 wt. % and about 0.5 wt. %.

Humectant

In preferred embodiments, the compositions can comprise one or more humectants. Preferred humectants, include, but are not limited to, hydroxyethyl urea, agarose, urea, sodium PCA, arginine PCA, fructose, glucose, glutamic acid, glycerin, diglycerin, honey, lactose, maltose, erythritol, polyethylene glycol, sorbitol, polyquats, polyglycerin-6, polyglycerin-10, methylpropanediol, 1,2-propanediol, dipropylene glycol, tri propylene glycol, 3-methylbutane-1,2-diol, pentylene glycol, 1,2-hexanediol, methyl gluceth-10, methyl gluceth-20, and mixtures thereof.

Preferably, the use dilution compositions can comprise from about 0 wt. % to about 5 wt. %, 0.05 wt. % to about 5 wt. % humectant, and most preferably from about 0.1 wt. % to about 5 wt. % humectant.

Preservative

In a preferred embodiment, the compositions comprise one or more preservatives. Preferred preservatives, include, phenolics, halogen compounds, metal derivatives, amines, alkanolamines, nitro derivatives, biguanides, analides, organosulfur and sulfur-nitrogen compounds, alkyl parabens, and other compounds.

Preferred phenolic compounds include, but are not limited to, pentachlorophenol, orthophenylphenol, chloroxylenol, p-chloro-m-cresol, p-chlorophenol, chlorothymol, m-cresol, o-cresol, p-cresol, isopropyl cresols, mixed cresols, phenoxyethanol, phenoxyethylparaben, phenoxyisopropanol, phenyl paraben, resorcinol, and derivatives thereof.

Preferred halogen compounds include, but are not limited to iodine-poly(vinylpyrrolidin-onen) complexes, and bromine compounds such as 2-bromo-2-nitropropane-1,3-diol, and derivatives thereof.

Preferred amines and nitro containing compounds include, but are not limited to, hexahydro-1,3,5-tris(2-hydroxyethyl)-s-triazine, dithiocarbamates such as sodium dimethyldithiocarbamate, and derivatives thereof.

Preferred biguanides include, but are not limited to, polyaminopropyl biguanide and chlorhexidine gluconate.

Preferred alkyl parabens include, but are not limited to, methyl, ethyl, propyl and butyl parabens.

Other optional preservatives include, but are not limited to, benzoic acid, sorbic acid, triclosan, chloroxylenol (parachloro meta-xylenol), caprylyl glycol, glycerol caprylate, ethylhexyl glycerin, benzoates, sorbates, or mixtures thereof.

When a preservative is included in the use dilution compositions, it is preferably in an amount from about 0.01 wt. % to about 2 wt. %, more preferably from about 0.1 wt. % to about 1.5 wt. %, and most preferably from about 0.2 wt. % to about 1 wt. %.

Secondary Foaming Agent

The compositions can optionally comprise one or more secondary foaming agents. Preferred secondary foaming agents, include, amphoteric surfactants, nonionic surfactants, and cationic surfactants. In a preferred embodiment, the compositions comprise one or more secondary foaming agents; in a more preferred embodiment the compositions comprise two or more secondary foaming agents. Suitable secondary foaming agents are discussed below.

If included in the use dilution compositions, the secondary foaming agent is preferably in a concentration of between about 0.1 wt. % and about 5 wt. %, preferably about 0.5 wt. % and about 4 wt. %, and more preferably between about 1 wt. % and about 2.5 wt. %.

Cationic Surfactants

Examples of cationic surfactants suitable as foaming agents include, but are not limited to, quaternized polysaccharides, alkyl polysaccharides, alkoxylated amines, alkoxylated ether amines, and mixtures thereof.

Cationic surfactants preferably include, more preferably refer to, compounds containing at least one long carbon chain hydrophobic group and at least one positively charged nitrogen. The long carbon chain group may be attached directly to the nitrogen atom by simple substitution; or more preferably indirectly by a bridging functional group or groups in so-called interrupted alkylamines and amido amines Such functional groups can make the molecule more hydrophilic and/or more water dispersible, more easily water solubilized by co-surfactant mixtures, and/or water soluble. For increased water solubility, additional primary, secondary or tertiary amino groups can be introduced or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The surfactant compounds classified as amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution. At pH levels less than 4, amine oxide type surfactants can also have some cationic character.

The simplest cationic amines, amine salts and quaternary ammonium compounds can be schematically drawn thus:

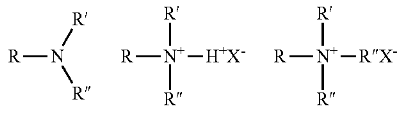

in which, R represents a long alkyl chain, R', R", and R"' may be either long alkyl chains or smaller alkyl or aryl groups or hydrogen and X represents an anion. The amine salts and quaternary ammonium compounds are preferred for practical use in this invention due to their high degree of water solubility.

The majority of large volume commercial cationic surfactants can be subdivided into four major classes and additional sub-groups known to those or skill in the art and described in "Surfactant Encyclopedia", *Cosmetics & Toiletries,* Vol. 104 (2) 86-96 (1989). The first class includes alkylamines and their salts. The second class includes alkyl imidazolines. The third class includes ethoxylated amines The fourth class includes quaternaries, such as alkylbenzyldimethylammonium salts, alkyl benzene salts, heterocyclic ammonium salts, tetra alkylammonium salts, and the like. Cationic surfactants are known to have a variety of properties that can be beneficial in the present compositions. These desirable properties can include detergency in compositions of or below neutral pH, antimicrobial efficacy, thickening or gelling in cooperation with other agents, and the like.

Examples of cationic surfactants includes the chloride, bromide, or methosulfate salts of alkyltrimethylammonium species where the alkyl group chain length is C8-C18, the preferred alkyl chain length is C8-16, and the most preferred alkyl chain length is C8-C14.

Nonionic Surfactants

The antimicrobial composition can contain a nonionic surfactant component that includes a detersive amount of nonionic surfactant or a mixture of nonionic surfactants. Typically, a nonionic surfactant has a hydrophobic region, such as a long chain alkyl group or an alkylated aryl group, and a hydrophilic group comprising an ethoxy and/or other hydrophilic moieties.

Examples of nonionic surfactants suitable as foaming agents include, but are not limited to, amine oxides, alcohol ethoxylates, fatty acid ethoxylates, alkyl phenol ethoxylate, monoalkonaolamide ethoxylates, sorbitan esters and their ethoxylated derivatives, ethoxylated fats and oils, amine ethoxylates, ethylene oxide-propylene oxide co-polymers, glycol esters, glycerol and polyglycerol esters, sucrose esters mono and polysaccharides surfactants, such as alkyl polyglucosides, alkyl alcohol ethoxylates, capped alkyl alcohol ethoxylates, fatty alcohol ethoxylate propoxylates, ethoxylated siloxane copolymers (PEG dimethicone) including alkyl capped, PEG/PPG dimethicones, mixtures thereof, or the like. Preferred substituted amides include, but are not limited to, glucosamides.

The secondary foaming agent can also comprise an alkyl amine oxide or alkyl ether amine oxide, hereto referred to a amine oxides. Amine oxides are a semi-polar type of nonionic surface active agents composed of tertiary amine oxides corresponding to the general formulas:

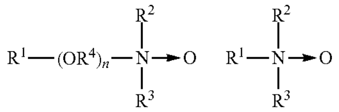

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene, a hydroxyalkylene group, or a alkylether group, containing 2 to 3 carbon atoms; and n ranges from 0 to about 20. An amine oxide can be generated from the corresponding amine and an oxidizing agent, such as hydrogen peroxide. If an amine oxide is included in the composition, it is preferably a C8-18 amine oxide.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylamine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

While amine oxides are often employed in dermal cleansers, it is preferred that they only be used in a small amount in these compositions due to their defatting properties, which can cause skin irritation and dryness. As such, in preferred embodiments, the antimicrobial compositions can be substantially free of an amine oxide surfactant or contain less than about 3 wt. %; more preferably, less than about 2 wt. %; still more preferably; less than about 1.5 wt. %, even more preferably; less than about 1 wt. %; yet more preferably less than about 0.5 wt. %; and most preferably less than about 0.1 wt. %.

Phospholipids and Phospholipid Derivatives

Phospholipid and/or phospholipid derivative surfactants can also be included. Preferred phospholipid derivatives include, but are not limited to, diester and triester phosphatides with multiple chain groups, and mixtures thereof. Preferred phospholipid surfactants include, but are not limited to coco PG-dimonium chloride phosphate, myristamidopropyl PG-dimonium chloride phosphate, linoleamidopropyl PG-dimonium chloride phosphate, stearamidopropyl PG-dimonium chloride phosphate, and mixtures thereof.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" Cosmetics & Toiletries, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Commercially prominent imidazoline-derived amphoterics that can be employed in the present compositions include for example: Cocoamphopropionate, Cocoamphocarboxypropionate, Cocoamphoglycinate, Cocoamphocarboxyglycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Suitable amphoteric surfactants include those derived from coconut products such as coconut oil or coconut fatty acid or the distilled fractions thereof. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+(CH_2—CH_2—CO_2Na)_2$—$CH_2$—$CH_2$—OH or $C_{12}$-alkyl-C(O)—N(H)—$CH_2$—$CH_2$—$N^+(CH_2—CO_2Na)_2$—$CH_2$—$CH_2$—OH. Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong" inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated. Notably, the zwitterionic surfactants are only compatible in minor amounts due to the anionic counter ion. Thus, if formulating with a zwitterionic surfactant, the zwitterionic surfactant should only be included in a minor concentration.

Preferred secondary foaming agents include, alkyl trimethyl ammonium chlorides, palmitamidopropyl trimonium chloride, diester phosphatides with multiple chain groups, triester phosphatides, coco PG-dimonium chloride phosphate, myristamidopropyl PG-dimonium chloride phosphate, linoleamidopropyl PG-dimonium chloride phosphate, stearamidopropyl PG-dimonium chloride phosphate, and mixtures thereof. Preferred alkyl trimethyl ammonium chlorides include, but are not limited to, C12-C14 alkyl trimethyl ammonium chlorides. A most preferred alkyl trimethyl ammonium chloride is lauryl trimethyl ammonium chloride.

Thickeners

The composition may optionally include a thickener. Examples of compatible thickeners include Guar, Hydroxypropyl Guar, Xanthan, Carrageenan, Karaya, Polyethylene Glycol (PEG), Cellulose Derivatives, including but not limited to hydroxyethyl cellulose, hydroxypropyl cellulose, hydroxylpropylmethtyl cellulose, alkyl modified hydroxyethyl cellulose, hydroxylethylpropyl, polyquaternium 10, Associative Thickeners including but not limited to hydrophobically modified ethoxylated urethanes (HEUR), polyethylene glycol dialkyl esters, PEG/PPG-450/50 trimethylolpropane dodecyl ether, Bis-C16-20 Isoalkoxy TMHDI/PEG-90 Copolymer, PEG-120 Methyl Glucose dioleate, PEG-18 Glceryl olieate/cocoate, sorbitan sesquicaprylate, and mixtures thereof.

Exemplary Embodiments of the Antimicrobial Compositions

The antimicrobial compositions can be prepared as a ready-to-use solution or a concentrated dilutable composition. Preferably, the compositions are liquids, which can be dispensed as a liquid, a foam, or by an aerosol dispenser.

Exemplary ready-to-use compositions are provided in Tables 1A through 1C. The ranges in each table should be considered to be modified by the word "about" as defined herein.

TABLE 1A

| Ingredients | First Exemplary Embodiment | Second Exemplary Embodiment | Third Exemplary Embodiment |
|---|---|---|---|
| L-Amino Acid | 0.075-2 wt. % or 5-150 mM | 0.1-1.8 wt. % or 10-120 mM | 0.2-1.5 wt. % or 20-100 mM |
| Antimicrobial Active | 0.01-2 wt. % | 0.05-1.5 wt. % | 0.1-1 wt. % |
| Carrier | 65-99.7 wt. % | 75-99.5 wt. % | 80-95 wt. % |
| Primary Foaming Agent | 0.1-5 wt. % | 0.5-4.5 wt. % | 1.0-4 wt. % |
| Additional Optional Ingredients | 0-15 wt. % | 0-12 wt. % | 0.01-10 wt. % |

TABLE 1B

| Ingredients | First Exemplary Embodiment (wt. %) | Second Exemplary Embodiment (wt. %) | Third Exemplary Embodiment (wt. %) |
|---|---|---|---|
| Antimicrobial Active | 0.01-2 | 0.05-1.5 | 0.1-1 |
| Carrier | 65-99.7 | 75-99.5 | 80-95 |
| Guerbet Alcohol Ethoxylate | 0.1-2 | 0.3-1.5 | 0.5-1.5 |
| Primary Foaming Agent | 0.1-5 | 0.5-4.5 | 1.0-4 |
| Additional Optional Ingredients | 0-15 | 0-12 | 0.01-10 |

TABLE 1C

| Ingredients | First Exemplary Embodiment | Second Exemplary Embodiment | Third Exemplary Embodiment |
|---|---|---|---|
| L-Amino Acid | 0.075-2 wt. % or 5-150 mM | 0.1-1.8 wt. % or 10-120 mM | 0.2-1.5 wt. % or 20-100 mM |
| Antimicrobial Active | 0.01-2 wt. % | 0.05-1.5 wt. % | 0.1-1 wt. % |
| Carrier | 65-99.7 wt. % | 75-99.5 wt. % | 80-95 wt. % |
| Guerbet Alcohol Ethoxylate | 0.1-2 wt. % | 0.3-1.5 wt. % | 0.5-1.5 wt. % |
| Primary Foaming Agent | 0.1-5 wt. % | 0.5-4.5 wt. % | 1.0-4 wt. % |
| Additional Optional Ingredients | 0-15 wt. % | 0-12 wt. % | 0.01-10 wt. % |

Additionally, the antimicrobial compositions can be prepared in liquid, gel, or solid concentrates, which would be subsequently diluted to the proper use concentration with a carrier either manually or by suitable equipment or an apparatus. Preferably concentrated compositions are between 2 to 10 times the concentration of the ready-to-use formulations ingredients, except the carrier.

Embodiments of concentrated compositions can be concentrated sufficiently to be diluted with a carrier (preferably comprising water) at a ratio of between about 1:1 and about 1:15. A concentrated composition that will be diluted at a ratio of about 1:15 will likely be substantially free of any added carrier. Other suitable dilution ratios include about 1:2, about 1:3, about 1:4, about 1:5, about 1:6, about 1:7, about 1:8, about 1:9, about 1:10, about 1:11, about 1:12, about 1:13, and about 1:14.

When provided as a liquid or gel concentrate composition, the concentrate can be diluted through dispensing equipment using aspirators, peristaltic pumps, gear pumps, mass flow meters, and the like. This liquid or gel concentrate embodiment can also be delivered in bottles, jars, dosing bottles, bottles with dosing caps, and the like. The liquid or gel concentrate composition can be filled into a multi-chambered cartridge insert that is then placed in a spray bottle or other delivery device filled with a pre-measured amount of water.

The antimicrobial compositions described herein provide a-cidal effect against microorganisms. In a preferred embodiment, the antimicrobial compositions provide a $Log_{10}$ reduction in microorganisms, including, but not limited to bacteria (gram positive and/or negative) and/or fungi, of greater than about 2.5 in about 15 seconds or less; more preferably greater than or equal to about 2.75 in about 15 seconds or less; most preferably greater than or equal to about 3 in about 15 seconds or less when tested according to ASTM E2315 Standard Guide for Assessment of Antimicrobial Activity Using a Time Kill Procedure. This is a dramatic improvement over existing formulations which often provide the similar log reductions in 60 seconds, 45 seconds, or at best 30 seconds. Given typical handwashing techniques employed by people, faster antimicrobial kill is important and needed.

While an understanding of the mechanism is not necessary to practice the present invention and while the present invention is not limited to any particular method of preparation, it is contemplated that, in some embodiments, the compositions can be prepared by combining the ingredients and mixing them until a homogeneous or near homogeneous mixture is prepared.

When provided as a liquid concentrate composition, the concentrate can be diluted through dispensing equipment using aspirators, peristaltic pumps, gear pumps, mass flow meters, and the like. This liquid concentrate embodiment can also be delivered in bottles, jars, dosing bottles, bottles with dosing caps, and the like. The liquid concentrate composition can be filled into a multi-chambered cartridge insert that is then placed in a spray bottle or other delivery device filled with a pre-measured amount of water.

The carrier used to dilute the concentrate will often be water or a water miscible carrier. When water is used, it can be available at the locale or site of dilution. In this respect, water for dilution may contain varying levels of hardness depending upon the locale. Service water available from various municipalities have varying levels of hardness. It is desirable to provide a concentrate that can handle the hardness levels found in the service water of various municipalities. The water of dilution that is used to dilute the concentrate can be characterized as hard water when it includes at least 1 grain hardness. It is expected that the water of dilution can include at least 5 grains hardness, at least 10 grains hardness, or at least 20 grains hardness.

It is expected that the concentrate will be diluted with the carrier in order to provide a use solution having a desired level of concentration of active ingredients. Preferably the concentrate can be diluted with the carrier at a weight ratio of at least about 1:1 and up to about 1:25.

In an alternate embodiment, the cleaning compositions may be provided as a ready-to-use ("RTU" or "use") composition. If the cleaning composition is provided as a RTU composition, a more significant amount of carrier is added to the cleaning composition as a diluent. It may be desirable to provide the concentrate (liquid or gel) in a flowable form so that it can be pumped or aspirated. It has been found that it is generally difficult to accurately pump a small amount of a liquid. It is generally more effective to pump a larger amount of a liquid. Accordingly, although it is desirable to provide the concentrate with as little carrier as possible in order to reduce transportation costs, it is also desirable to provide a concentrate that can be dispensed accurately.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only and are non-limiting. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The materials used in the following examples are provided herein:

Amino acids: L-Histidine, L-Glycine, L-Leucine, L-Glutamine, L-Arginine

Benzalkonium Chloride: An antimicrobial agent.

Capryloyl/Caproyl Methyl Glucamide: A nonionic surfactant, used as a foaming agent.

Citric acid: Used to adjust pH.

Cocamide Diethanolamine A nonionic surfactant, used as a foaming agent.

Cocamidopropyl PG-Dimonium Chloride Phosphate: A quaternary ammonium salt, used as a foaming agent.

Hexylene Glycol: A carrier agent.

Hydroxyethylcellulose: A foam structure enhancing agent.

Glycerin: A humectant.

Guerbet Alcohol: A $C_{10}$ Guerbet alcohol ethoxylate with 3-6 EO groups

Laurtrimonium Chloride: A quaternary ammonium salt, used as a foaming agent.

Methyl Gluceth-20: A humectant.

Palmitamidopropyltrimonium Chloride: A quaternary ammonium salt, used as a foaming agent.

Phenoxyethanol: A preservative.

Sodium hydroxide: Used to adjust pH.

Trisodium Dicarboxymethyl Alaninate ($Na_3MGDA$): A chelant.

The experiments described in Examples 1-3 were performed using the exemplary antiseptic formulations provided in Table 2. Additional exemplary antiseptic formulations are provided in Table 6 and described in Example 4. These formulations can be prepared as a ready-to-use solution or a concentration dilutable composition. The ranges in each table should be considered to be modified by the word "about" as defined herein.

TABLE 2

Exemplary Antiseptic Formulations

| Component | Formulation (wt-%) | | | | | |
|---|---|---|---|---|---|---|
| | 1a | 1b | 1c | 1d | 1e | 1f |
| Antimicrobial Active | 0.1-1 | 0.1-1 | 0.1-1 | 0.1-1 | 0.1-1 | 0.1-1 |
| Carrier | 85-99 | 85-99 | 85-99 | 85-99 | 85-99 | 85-99 |
| Primary Foaming Agent | 1-4 | 1-4 | 1-4 | 1-4 | 1-4 | 1-4 |
| Exemplary Guerbet Alcohol | | | | | 0.5-1.5 | 0.5-1.5 |
| L-Histidine (40 mM) | | 0.2-1.5 | | | | 0.2-1.5 |
| L-Glycine (40 mM) | | | 0.2-1.5 | | | |
| L-Arginine (40 mM) | | | | 0.2-1.5 | | |
| Secondary Foaming Agent | 1-4 | 1-4 | 1-4 | 1-4 | 1-4 | 1-4 |
| Humectant | 0.1-2.5 | 0.1-2.5 | 0.1-2.5 | 0.1-2.5 | 0.1-2.5 | 0.1-2.5 |
| Preservative | 0.2-1 | 0.2-1 | 0.2-1 | 0.2-1 | 0.2-1 | 0.2-1 |
| Chelant | 0.1-0.4 | 0.1-0.4 | 0.1-0.4 | 0.1-0.4 | 0.1-0.4 | 0.1-0.4 |
| Foam Structure Enhancing Agent | 0.03-2 | 0.03-2 | 0.03-2 | 0.03-2 | 0.03-2 | 0.03-2 |
| pH Adjuster | qs | qs | qs | qs | qs | qs |

In Examples 1-4, the survival of *Serratia marcescens* exposed to an antimicrobial test composition was measured using in vitro Time Kill testing, based on a modified version of ASTM E 2315 Standard Guide for Assessment of Antimicrobial Activity Using a Time Kill Procedure. Utilizing this method, the inoculum is prepared by growing a microbial culture using a D/E agar medium. The microbial population then is washed from the agar with sterile physiological saline and the population of the microbial suspension is adjusted to around $10^8$ colony forming units (cfu) per ml. An aliquot of the test formula, or a dilution thereof, is brought into contact with this known population of bacteria at ambient temperature. The test composition is neutralized after a set amount of time, which arrests the antimicrobial activity of the test sample. Under the ASTM that set amount of time is 30 seconds; however, for our testing this was modified to assess the log reduction after 15 seconds. The log reduction from the original bacteria population is calculated using the following formula:

$$\log_{10} \text{reduction} = \log_{10}(\text{control}) - \log_{10}(\text{test sample survivors})$$

Each test was performed in duplicate and the average log reduction reported.

Example 1

The efficacy of Formulations 1a, 1b, 1c, and 1d on the log reduction of *S. marcescens* were tested at various pH levels at a 15 second contact time. In each instance, citric acid and/or sodium hydroxide were added quantum satis to maintain the various tested pH levels at 6.5, 8.5, and 9.6. The results are shown in FIG. 1 as well as in Table 3 below. As shown above in Table 1, exemplary antiseptic compositions represented by Formulations 1b, 1c, and 1d all contain a different amino acid, whereas Formulation 1a represents an exemplary quaternary antiseptic composition that does not contain any amino acids. A difference of 0.5 log reduction between the formulations were considered significant.

TABLE 3

Impact of Amino Acids on Microbial Efficacy

| pH | *S. marcescens* Efficacy ($Log_{10}$ Reduction) | | | |
|---|---|---|---|---|
| | 1a (No Amino Acid) | 1b (+His) | 1c (+Gly) | 1d (+Arg) |
| pH 6.5 | 2.66 | 3.26 | 3.28 | 3.51 |
| pH 8.5 | 3.34 | 4.61 | 4.25 | 3.73 |
| pH 9.6 | 3.85 | 5.71 | 5.71 | 5.56 |

As shown in the results above, the formulations containing an amino acid were more effective against *S. marcescens* and resulted in a higher log reduction than Formulation 1a, which did not contain an amino acid. At a pH of 6.5, all formulations exhibited relatively similar log reduction. However, as pH increased, all formulations exhibited a higher log reduction of *S. marcescens,* with the formulations containing histidine, glycine, and arginine exhibiting a drastic increase in log reduction compared to Formulation 1a.

Example 2

Figure 2:
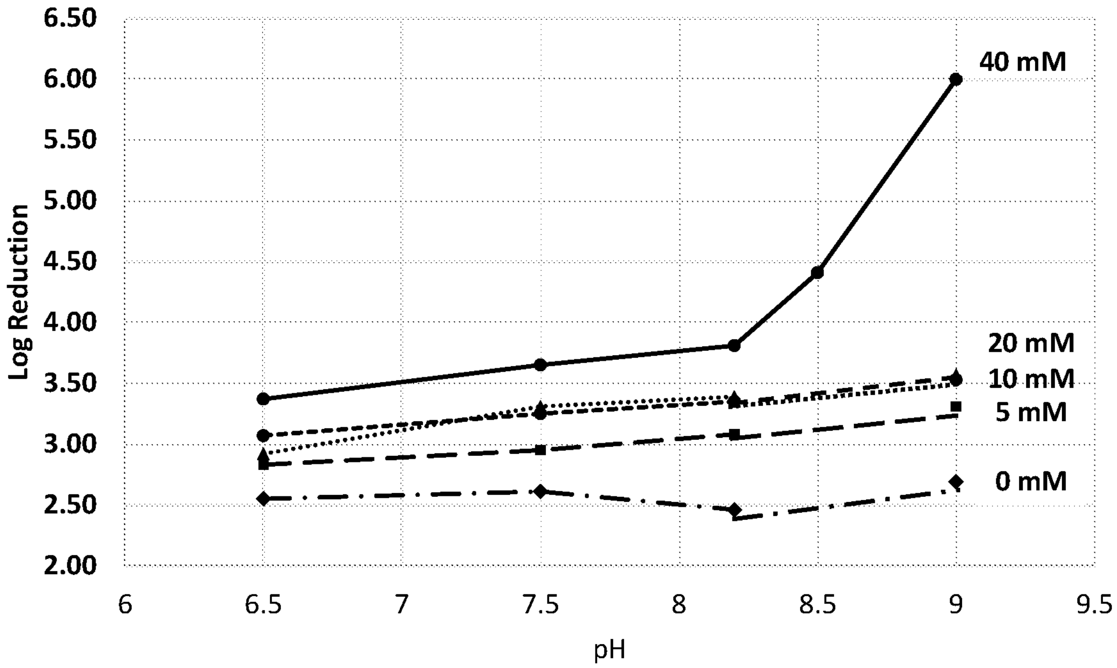
FIG. 2 shows a line graph comparing antimicrobial performance of an exemplary antimicrobial composition having various concentrations of L-histidine at various pH levels. The Figure is representative of the data provided in Table 3 of Example 2.

Various concentrations of histidine were evaluated for their ability to enhance the log reduction of *S. marcescens* at different pH levels after a 15 second contact time. Formulation 1a served as the base for all samples tested, with varying concentrations of L-histidine added to Formulation 1a (0 mM, 5 mM, 10 mM, 20 mM, and 40 mM). The results are shown in FIG. 2 as well as in Table 4 below.

TABLE 4

Effect of Amino Acid Concentration as a Function of pH

| Formulation | *S. marcescens* Efficacy ($Log_{10}$ reduction) | | | |
|---|---|---|---|---|
| | pH 6.5 | pH 7.5 | pH 8.2 | pH 9 |
| Formulation 1a | 2.55 | 2.61 | 2.46 | 2.69 |
| Formulation 1a + 5 mM His | 2.83 | 2.95 | 3.08 | 3.31 |
| Formulation 1a + 10 mM His | 3.07 | 3.25 | 3.35 | 3.53 |

TABLE 4-continued

| Effect of Amino Acid Concentration as a Function of pH | | | | |
|---|---|---|---|---|
| | *S. marcescens* Efficacy ($Log_{10}$ reduction) | | | |
| Formulation | pH 6.5 | pH 7.5 | pH 8.2 | pH 9 |
| Formulation 1a + 20 mM His | 2.92 | 3.31 | 3.39 | 3.57 |
| Formulation 1a + 40 mM His | 3.37 | 3.65 | 3.81 | >6.00 |

As shown in FIG. 2, as the concentration of the amino acid increased, the corresponding log reduction increased as well. However, as the pH became more alkaline, the sample with a concentration of 40 mM of histidine exhibited a drastic increase in log reduction of *S. marcescens* in comparison to the samples with a lower concentration of amino acid.

Example 3

Figure 3:
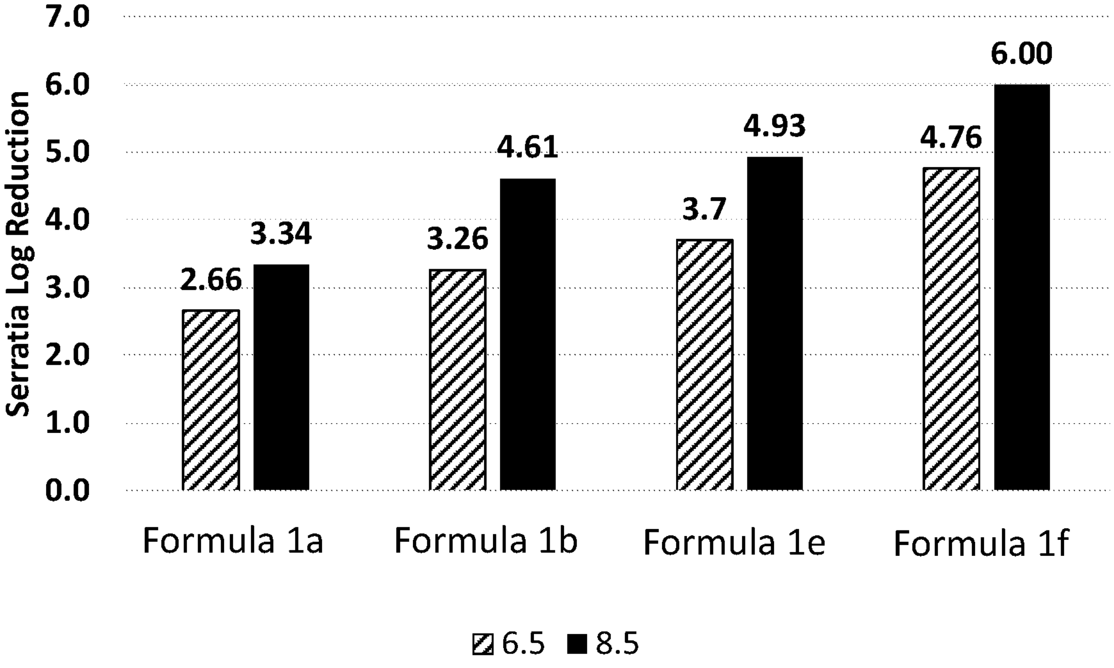
FIG. 3 shows a bar graph comparing antimicrobial performance of an exemplary antimicrobial composition containing no amino acid against various exemplary antimicrobial compositions containing either L-histidine, a guerbet alcohol, or both L-histidine and a guerbet alcohol at a pH of 6.5 or 8.5. The Figure is representative of the data provided in Table 4 of Example 3.

Various formulations were tested to evaluate the efficacy of adding an exemplary $C_{10}$ guerbet alcohol ethoxylate in addition to an amino acid on the log reduction of *S. marcescens* at various pH levels and at a 15 second contact time. Formulation 1b (exemplary quaternary antiseptic composition) was compared against Formulation 1b (exemplary antiseptic composition with L-histidine), Formulation 1e (exemplary antiseptic composition with a guerbet alcohol), and Formulation 1f (exemplary antiseptic composition with a guerbet alcohol and L-histidine). In each instance, citric acid and/or sodium hydroxide were added quantum satis to maintain the various tested pH levels at 6.5 and 8.5. The results are shown in FIG. 3 as well as Table 5 below. A log reduction equal to or greater than 6 indicated the attainment of complete kill against *S. marcescens*.

TABLE 5

| Synergistic Effect from Guerbet Alcohol Ethoxylate and Amino Acid | | | | |
|---|---|---|---|---|
| | *S. marcescens* Efficacy ($Log_{10}$ Reduction) | | | |
| pH | 1a (No Amino Acid) | 1b (+His) | 1e (+Guerbet alcohol) | 1d (+Guerbet alcohol + His) |
| pH 6.5 | 2.66 | 3.26 | 3.70 | 4.76 |
| pH 8.5 | 3.34 | 4.61 | 4.93 | >6.00 |

As shown in Table 5, the addition of the guerbet alcohol exhibited similar or better log reduction than the formulation with no amino acid or the formulation with the addition of histidine. However, the addition of both a guerbet alcohol and an amino acid resulted in a surprising synergistic effect and subsequently lead to a significantly higher level of biocidal activity. This synergistic effect was observed under both pH levels of 6.5 and 8.5. Under a pH of 8.5, the formulation containing both a guerbet alcohol and histidine was able to achieve complete kill against *S. marcescens* with a 15 second contact time.

Example 4

Additional formulations were evaluated to compare varying combinations of adding a guerbet alcohol to different amino acids. The formulations are presented in Table 6 below.

TABLE 6

| Exemplary Antiseptic Formulations | | | | | | | | | | |
|---|---|---|---|---|---|---|---|---|---|---|
| | Formulation (wt-%) | | | | | | | | | |
| Component | 2a | 2b | 3a | 3b | 4a | 4b | 5a | 5b | 6a | 6b |
| Antimicrobial Active | 0.1-1 | 0.1-1 | 0.1-1 | 0.1-1 | 0.1-1 | 0.1-1 | 0.1-1 | 0.1-1 | 0.1-1 | 0.1-1 |
| Carrier | 85-99 | 85-99 | 85-99 | 85-99 | 85-99 | 85-99 | 85-99 | 85-99 | 85-99 | 85--99 |
| Primary Foaming Agent | 1-4 | 1-4 | 1-4 | 1-4 | 1-4 | 1-4 | 1-4 | 1-4 | 1-4 | 1-4 |
| Exemplary Guerbet Alcohol | | 0.5-1.5 | | 0.5-1.5 | | 0.5-1.5 | | 0.5-1.5 | | 0.5-1.5 |
| L-Histidine | 0.2-1.5 | 0.2-1.5 | | | | | | | | |
| L-Lycine | | | 0.2-1.5 | 0.2-1.5 | | | | | | |
| L-Leucine | | | | | 0.2-1.5 | 0.2-1.5 | | | | |
| L-Glutamine | | | | | | | 0.2-1.5 | 0.2-1.5 | | |
| L-Arginine | | | | | | | | | 0.2-1.5 | 0.2-1.5 |
| Secondary Foaming Agent | 0.03-2 | 0.03-2 | 0.03-2 | 0.03-2 | 0.03-2 | 0.03-2 | 0.03-2 | 0.03-2 | 0.03-2 | 0.03-2 |
| Humectant | 0.1-2.5 | 0.1-2.5 | 0.1-2.5 | 0.1-2.5 | 0.1-2.5 | 0.1-2.5 | 0.1-2.5 | 0.1-2.5 | 0.1-2.5 | 0.1-2.5 |
| Preservative | 0.2-1 | 0.2-1 | 0.2-1 | 0.2-1 | 0.2-1 | 0.2-1 | 0.2-1 | 0.2-1 | 0.2-1 | 0.2-1 |
| Chelant | 0.03-2 | 0.03-2 | 0.03-2 | 0.03-2 | 0.03-2 | 0.03-2 | 0.03-2 | 0.03-2 | 0.03-2 | 0.03-2 |
| pH Adjuster | qs | qs | qs | qs | qs | qs | qs | qs | qs | Qs |

Figure 4:
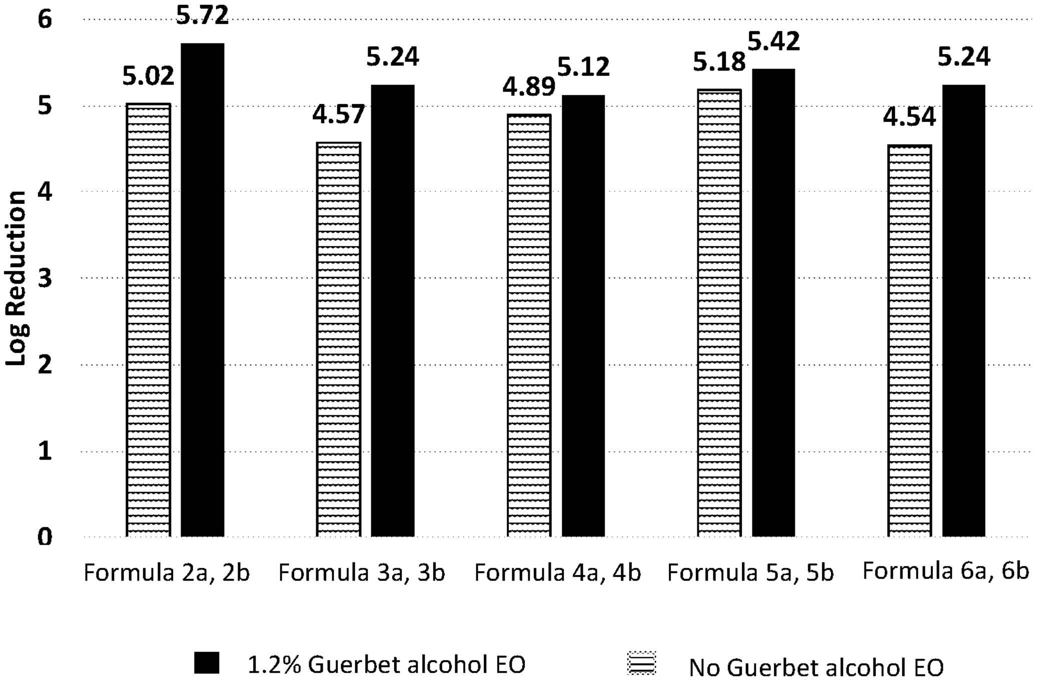
FIG. 4 shows a bar graph comparing antimicrobial performance of various exemplary antimicrobial compositions containing either an amino acid, or both an amino acid plus a guerbet alcohol at a pH of 7.5. The Figure is representative of the data provided in Table 6 of Example 4.

Further, the efficacy of each exemplary antiseptic composition was evaluated by measuring the log reduction of *S. marcescens* with a 15 second contact time. As shown in Table 6, Formulations 2a, 3a, 4a, 5a, and 6a all contain an amino acid, but do not contain a Guerbet alcohol. Conversely, Formulations 2b, 3b, 4b, 5b, and 6b all contain an amino acid, but also contain a Guerbet alcohol. All formulations were tested at a pH of 7.5. The results are shown in FIG. 4 and Table 7.

TABLE 7

| Effect of Amino Acid with Guerbet Alcohol Synergy | | | | | | | | | | |
|---|---|---|---|---|---|---|---|---|---|---|
| | Histidine | | Lysine | | Leucine | | Glutamine | | Arginine | |
| | 2a | 2b | 3a | 3b | 4a | 4b | 5a | 5b | 6a | 6b |
| *S. marcescens* Efficacy ($Log_{10}$ reduction) | 5.02 | >5.72 | 4.57 | 5.24 | 4.89 | 5.12 | 5.18 | 5.42 | 4.54 | 5.24 |

As shown in Table 7, the inclusion of an amino acid exhibited effective log reduction for all formulations at a pH of 7.5. However, the addition of a guerbet alcohol in addition to the amino acid resulted in a surprising synergistic effect across all amino acids, and subsequently lead to a significantly higher level of biocidal activity. These results illustrate the beneficial synergistic effect of combining a guerbet alcohol with an amino acid in microbial log reduction, even under less alkaline pH conditions.

Example 5

The survival of *Serratia marcescens* exposed to an antimicrobial test composition was measured using ex vivo testing, based on a modified version of ASTM E 2897 Standard Guide for the Evaluation of the Effectiveness of Hand Hygiene Topical Antimicrobial Products using ex vivo Porcine Skin. Utilizing this method, the inoculum is prepared by growing a microbial culture using Tryptic Soy Broth. The microbial population then is washed from the agar with sterile physiological saline and the population of the microbial suspension is adjusted to around $10^7$ colony forming units (cfu) per ml. Porcine skin was stored at −20° C. until ready to use at which point the skin was removed from the freezer and allowed to thaw prior to being cut into 5 cm square pieces.

An aliquot of the inoculum is brought into contact with the two square pieces of porcine skin with this known population of bacteria at ambient temperature. The volume of the inoculum is determined by:

$$\text{Volume of liquid applied} = \frac{V1_{volume\ desired\ on\ hands} * A1_{surface\ area\ of\ pigskin}}{A2_{surface\ area\ of\ hands}}$$

The two porcine skin pieces were rubbed together to evenly distribute the inoculum and allowed to dry for 30 minutes.

An aliquot of the test formula, or a dilution thereof, is applied on the pair of porcine skin, with volume as determined by the above equation. The porcine skin pair is rubbed, rinsed, and dried together to mimic actions while using hand hygiene products. The test composition is neutralized after 60 seconds, which arrests the antimicrobial activity of the test sample. The neutralizer (also the sampling fluid) are then extracted to be incubated as the test sample survivors. The log reduction from the original bacteria population is calculated using the following formula:

$$\log_{10}\text{ reduction}=\log_{10}(\text{control})-\log_{10}(\text{test sample survivors})$$

Each test was performed in duplicate and the average log reduction reported. The test compositions employed are provided below in Table 8 and the results are provided in Table 9.

TABLE 8

| | Formulation (wt-%) | |
|---|---|---|
| Component | 7a | 7b |
| Antimicrobial Active | 0.1-1 | 0.1-1 |
| Carrier | 85-99 | 85-99 |
| Primary Foaming Agent | 1-4 | 1-4 |
| L-amino acid (40 mM) | | 0.2-1.5 |
| Secondary Foaming Agent | 1-4 | 1-4 |
| Humectant | 0.1-2.5 | 0.1-2.5 |
| Preservative | 0.2-1 | 0.2-1 |
| Chelant | 0.1-0.4 | 0.1-0.4 |
| Foam Structure Enhancing Agent | 0.03-2 | 0.03-2 |
| pH Adjuster | Qs | Qs |

TABLE 9

| Organism/Formula | Avg. Log Survivor | Avg. Log Reduction |
|---|---|---|
| *Serratia marcescens* (ATCC 14756) Microbial Control | 7.88 | — |
| Formula 7a | 6.59 | 1.29 |
| Formula 7b | 6.20 | 1.68 |
| Hibiclens 4% CHG (positive control) | 6.31 | 1.57 |
| Saline (negative control) | 7.06 | 0.82 |

This testing was performed based on the current Food and Drug Administration (FDA) assessment where a test formulation is tested against a negative control (saline) and Hibiclens 4% CHG as a positive control. According to the FDA assessment standard, the test composition is supposed to not be inferior to the positive control and must be superior to the negative control. The test compositions of Formulation 7a and 7b were identical except for the inclusion of an exemplary L-amino acid in Formulation 7b. As can be seen from the test results in Table 9, Formulation 7b was not inferior to the Hibiclens (and in fact provided a 0.1 log improvement, which is considerable under these test conditions) and was superior to the negative control. Additionally, as can be seen from the test, it was surprisingly found that the exact composition only with the addition of an L-amino acid provided an increased log reduction of about 0.4, i.e., Formulation 7a (without amino acid) had an average log reduction on porcine skin of about 1.29 whereas Formulation 7b (with amino acid) had an average log reduction of about 1.68. This demonstrates the unexpected results attributable to the synergistic behavior of the formulation when an L-amino acid is included.

The inventions being thus described, it will be obvious that the same may be varied in many ways. Such variations are not to be regarded as a departure from the spirit and scope of the inventions and all such modifications are intended to be included within the scope of the following claims.

What is claimed is:

1. An antimicrobial composition comprising:

from about 0.1 wt. % to about 1 wt. % of an antimicrobial active compound comprising one or more of the following benzalkonium chloride, benzethonium chloride, chlorhexidine gluconate, and mixtures thereof, wherein the antimicrobial active compound has antimicrobial activity toward Gram positive and/or Gram negative microorganisms;

from about 1 wt. % to about 4 wt. % of a primary foaming agent, wherein the primary foaming agent comprises a C8-C16 alkanolamide, a glucosamide, or a mixture thereof;

from about 0.5 wt. % to about 1.5 wt. % of a $C_8$-$C_{12}$ Guerbet alcohol ethoxylate;

from about 0.1 wt. % to about 5 wt. % of a secondary foaming agent; wherein the secondary foaming agent comprises an alkyl trimethyl ammonium chloride;

from about 20 mM to about 100 mM of an L-amino acid comprising L-histidine, L-glycine, L-arginine, or a combination thereof; and from about 65 wt. % to about 99.7 wt. % of a carrier comprising hexylene glycol; wherein the composition has a pH between about 9 and about 9.6.

2. The antimicrobial composition of claim 1, wherein the C8-C16 alkanolamide is a cocamide, a lauramide, a myristamide, a soyamide, or a mixture thereof.

3. The antimicrobial composition of claim 1, wherein the primary foaming agent comprises cocamide monoethanolamine, cocamide diethanolamine, cocamide methyl monoethanolamine, cocamide monoisopropanolamine, cocamide diisopropanolamine, lauramide MEA, lauramide DEA, lauramide MIPA, myristamide MEA, myristamide DEA, soyamide DEA, a C8-C16 glucosamide, or a mixture thereof; wherein the C8-C16 glucosamide comprises capryloyl/caproyl methyl glucosamide, cocoyl methyl glucamide, lauroyl/myristoyl methyl glucamide, or a mixture thereof.

4. The antimicrobial composition of claim 1, wherein the secondary foaming agent further comprises an amine oxide, cocamidopropyl betaine, palmitamidopropyl trimonium chloride, a phospholipid surfactant, a phospholipid derivative surfactant, or a mixture thereof.

5. The antimicrobial composition of claim 1, wherein the L-amino acid is L-histidine.

6. The antimicrobial composition of claim 1, further comprising between about 0.01 wt. % and about 15 wt. % of an additional functional ingredient; wherein the additional functional ingredient comprises a chelant, an emollient, a foam structure enhancing agent, a fragrance, a humectant, a preservative, or a combination thereof.

7. The antimicrobial composition of claim 1, wherein the composition is a liquid which can be dispensed as a liquid, a foam, or by an aerosol dispenser.

8. An antimicrobial composition comprising:

from about 0.1 wt. % to about 1 wt. % of an antimicrobial active compound comprising benzalkonium chloride, wherein the antimicrobial active compound has antimicrobial activity toward Gram positive and/or Gram negative microorganisms;

from about 1 wt. % to about 4 wt. % of a primary foaming agent, wherein the primary foaming agent comprises capryloyl/caproyl methyl glucamide, cocamide diethanolamine, cocamidopropryl PG-dimonium chloride phosphate, laurtrimonium chloride, palmitamidopropyltrimonium chloride, or a mixture thereof;

from about 20 mM to about 100 mM of an L-amino acid comprising L-histidine, L-glycine, L-arginine, or a combination thereof;

from about 0.5 wt. % to about 1.5 wt. % of a Cio Guerbet alcohol ethoxylate with 3-6 EO groups;

from about 0.1 wt. % to about 5 wt. % of a secondary foaming agent; wherein the secondary foaming agent comprises an alkyl trimethyl ammonium chloride; and from about 65 wt. % to about 99.7 wt. % of a carrier comprising hexylene glycol; wherein the composition has a pH between about 9 and about 9.6.

9. The antimicrobial composition of claim 8, wherein the L-amino acid is L-glycine.

10. The antimicrobial composition of claim 8, wherein the secondary foaming agent further comprises an amine oxide, cocamidopropyl betaine, palmitamidopropyl trimonium chloride, a phospholipid surfactant, a phospholipid derivative surfactant, or a mixture thereof.

11. The antimicrobial composition of claim 8, wherein the composition provides a log reduction of *S. marcescens* of greater than about 4 in about 15 seconds in an in vitro assay.

12. A method of cleaning a surface comprising:

contacting a surface with the antimicrobial composition of claim 1, wherein the surface is skin.

13. The method of claim 12, wherein the antimicrobial composition is dispensed as a liquid, a foam, or by an aerosol dispenser.

14. The method of claim 13, wherein the method further comprises rinsing the surface.

15. The method of claim 12, wherein the antimicrobial composition is a concentrated antimicrobial composition and the method further comprises diluting the concentrated antimicrobial composition prior to the contacting step.

16. The method of claim 15, wherein the concentrated antimicrobial composition is a liquid, gel, or solid.

* * * * *